United States Patent [19]

Imagawa et al.

[11] Patent Number: 4,942,122
[45] Date of Patent: Jul. 17, 1990

[54] AIDS PROGNOSIS TEST DETECTING THE PRESENCE OF ANTIBODIES INHIBITING HIV REVERSE TRANSCRIPTASE

[75] Inventors: David T. Imagawa, Rancho Palos Verdes; Moon H. Lee, Hacienda Heights; Kouichi Sano, Gardena, all of Calif.

[73] Assignee: Research Education Institute, Inc., Torrance, Calif.

[21] Appl. No.: 17,450

[22] Filed: Feb. 24, 1987

[51] Int. Cl.$^5$ .......................................... G01N 33/569
[52] U.S. Cl. .......................................... 435/5; 435/6; 435/7; 435/810
[58] Field of Search ........................................ 435/5-7, 435/810

[56] References Cited

PUBLICATIONS

Sarin et al., "Neutralization of HTLV-III/LAV Replication by Antiserum to Thymosin $\beta_1$", Science, vol. 232 (1986) 1135–1137.

Taylor et al., "Prognostically Significant Classification of Immune Changes in Aids with Kaposi's Sarcoma", Blood, 67 (1986) 666–671.

Sano et al., "Antibody that Inhibits Immunodeficiency Virus Reverse Transcriptase and Association with Inability to Isolate Virus", Journal of Clinical Microbiology, 25 (1987):2415–2417.

Steimer et al., "Recombinant Polypeptide from the Endonuclease Region of the Acquired Immune Deficiency Syndrome Retrovirus Polymerase (pol) Gene Detects Serum Antibodies in Most Infected Individuals", Journal of Virology, 58 (1986):9–16.

Chandra et al., "Serological Relationship Between Reverse Transcriptases from Human T-Cell Lymphotropic Viruses Defined by Monoclonal Antibodies", FEBS Letters, 200 (1986):327–332.

B. F. Polk et al.: "Predictors of the Acquired Immunodeficiency Syndrome Developing in a Cohost of Seropositive Homosexual Men" New England Journal of Medicine; 316: 61 (1987).

J. Laurence et al. "Characterization and Clinical Association of Antibody Inhibitory to HIV Reverse Transcriptase Activity"; Science, 235, 1501–1504 (1987).

*Primary Examiner*—Christine M. Nucker
*Attorney, Agent, or Firm*—Drucker & Sommers

[57] ABSTRACT

A kit and a method for detecting the presence of an antibody inhibiting HIV (the AIDS virus) reverse transcriptase. The amount of antibody inhibiting HIV reverse transcriptase present in the body fluids of a patient known to be immunopositive for HIV gives the clinician a means to form a prognosis for each individual case.

11 Claims, No Drawings

AIDS PROGNOSIS TEST DETECTING THE PRESENCE OF ANTIBODIES INHIBITING HIV REVERSE TRANSCRIPTASE

BACKGROUND OF THE INVENTION

1. Field of the Invention

This invention relates to diagnostic tests for viral diseases, and particularly diagnostic tests for AIDS.

2. Prior Art

Acquired Immune Deficiency Syndrome (AIDS) is caused by a retrovirus that is transmitted primarily by blood and blood products. In the United States the disease has occurred in certain groups more than others: homosexuals, Haitians, recipients of blood transfusions, and intravenous drug abusers. Epidemiologists now believe that the disease is more infectious and more widespread than heretofore believed.

Not all patients who are immunopositive for the AIDS virus, hereinafter HIV (Human Immunodeficiency Virus), develop any symptoms. Indeed, frequently the virus is not detected in patients who are immunopositive for HIV. The clinician therefore needs a diagnostic tool that would allow rapid determination of the prognosis of a patient who is immunopositive for HIV.

The AIDS virus has been identified and extensively characterized. *Science*, Volume 224, (1984) has four articles about the identification of an isolate of HIV, identified therein as HTLV-III.

The viral genome has been completely mapped. One extensive mapping is shown in *Nature*, 313:277–284 (1985).

HIV is a retrovirus; that is, a virus that uses RNA as its genetic material instead of DNA and must produce a DNA equivalent of the RNA gene to replicate. Because of its unusual mode of replication, one enzyme that the virus must code for is reverse transcriptase. Reverse transcriptase is the enzyme that transcribes the genetic code from the viral RNA into viral DNA within the host cell. This is a necessary step in the replication cycle of the virus.

The reverse transcriptase for HTLV-III/LAV is described in *Science*, Volume 231, page 1289 (1986). *Virology*, volume 147, pages 326–335 (1985), characterizes reverse transcriptase and describes optimal conditions for its detection.

The reverse transcriptase for HIV usually provokes a strong immune response in healthy humans. It has now been discovered that one can make a prognosis about the future course of the disease in a given patient, who is known to be immunopositive for HIV, by detecting antibodies that inhibit the action of the reverse transcriptase. If these antibodies inhibiting the reverse transcriptase are present, the prognosis is good. However, if the individual does not have antibodies for the reverse transcriptase, the prognosis is poor. Such an individual may develop the full range of AIDS-related symtoms, which may lead to the death of the individual.

SUMMARY OF THE INVENTION

An aspect of the present invention is a kit for developing a prognosis for a patient known to be exposed to HIV comprising:

(1) a solution of HIV reverse transcriptase;
(2) a suitable primed RNA template;
(3) a nucleoside triphosphate for synthesis of DNA;
(4) a positive sera control containing a known amount of antibody inhibiting HIV reverse transcriptase; and
(5) a negative sera control containing no antibodies to HIV.

A further aspect of the present invention is a method of developing a prognosis for a patient known to be immunopositive for HIV comprising:

quantitatively detecting the amount of an antibody inhibiting HIV reverse transcriptase in said patients body fluid.

A further aspect of the present invention is a method of treating diseases caused by HIV comprising:

administering a pharmaceutically acceptable amount of an antibody to HIV reverse transcriptase to a patient having disease symptoms caused by HIV.

DETAILED DESCRIPTION OF THE INVENTION

Definitions

As used herein, the virus that causes AIDS and AIDS-related symptoms will be identified as Human Immuno-deficiency Virus (HIV). HTLV-III and LAV can be thought of as specific isolates of HIV. Despite the confusion in the nomenclature, most researchers are convinced that the viruses identified by these different designations are, in fact, varients of the same virus and that they all cause AIDS.

As used herein, "AIDS" (Acquired Immune Deficiency Syndrome) will refer to the clinically definable disease defined by the presence of opportunistic infections, such as Kaposi's sarcoma, pneumocystis carinii pneumonia, and the like.

As used herein "pre-AIDS" will refer to severely depressed immune response in patients positive for HIV, but not so serious as to be diagnosed as AIDS.

As used herein, "HIV reverse transcriptase" will mean that enzyme that is produced by the naturally occurring virus to transcribe the viral RNA into DNA. HIV reverse transcriptase will be used herein to denote the enzyme regardless of the source of the enzyme. Any variant of HIV reverse transcriptase, for example, similar reverse transcriptase that may have one or more amino acid substitutions, can be considered HIV reverse transcriptase if the virus that produces it is considered to be a variant of HIV. The enzyme can be produced naturally by the virus or artificially by such techniques as genetic engineering and the like.

As used herein, "an antibody inhibiting HIV reverse transcriptase" means any antibody to HIV reverse transcriptase that stops or inhibits the enzymatic action of HIV reverse transcriptase. It will be appreciated that many different antibodies can be produced by the human immune response to HIV reverse transcriptase, but most antibodies produced will not inhibit the action of HIV reverse transcriptase. This invention relates only to those antibodies that inhibit the mode of action of HIV reverse transcriptase. It will also be appreciated that many different specific antibodies may inhibit HIV reverse transcriptase. All such antibodies, and all combinations of such antibodies, are the subject of this invention.

As used herein, "immunopositive for HIV" means that a given patient will have detectable amounts of antibodies for HIV in his blood, regardless if the virus can be isolated from his blood or if he has any overt symptoms of disease.

As used herein, "kit" will refer to a simply packaged and easily useable reagents for the detection of the presence of an antibody inhibiting HIV reverse transcriptase. The precise number of reaction tubes, their holders, and so forth, are choices that can be easily made by one skilled in the art.

As used herein, the term "RNA template" will refer to a RNA polymer that is usable in the apparatus and method of this invention. The preferred RNA template is polyadenylic acid (hereinafter "poly rA"). Primed poly rA will, in the presence of reverse transcriptase and thymidine 5'triphosphate (hereinafter dTTP), and the absence of an antibody inhibiting HIV reverse transcriptase produce polythymidylic acid (hereinafter "poly dT").

As used herein "primed RNA template" will refer to a long strand of RNA with a short complementary strand of DNA at to the 3-OH' end. Typically the DNA will be about 12 to 18 bases long. A particulary preferred primed RNA template is polyadenylic acid: oligothymidylic acid (hereinafter "poly rA.oligo dT").

As used herein, the "nucleoside triphosphate for synthesis of DNA" can be any deoxyribonucleoside triphosphate that results in the detection of HIV reverse transcriptase. A preferred nucleoside triphosphate, and the only one that will work if the RNA template is poly rA, is dTTP. The dTTP can be radiolabelled with tritium or with any other material which will detect DNA product, such as biotin-avidin enzyme. In the prognosis test of the present invention the absence of an antibody inhibiting HIV reverse transcriptase can be inferred by the synthesis and presence of radiolabelled poly dT. Conversely, the presence of the antibody can be inferred by no synthesis and the absence of radiolabelled poly dT.

As used in the specification, a "positive sera control" will be a solution with a known amount of reverse transcriptase inhibiting antibody.

As used herein, a "negative sera control" will be normal human serum with no antibodies to any HIV-related proteins.

As used herein, "body fluid" can be any fluid contained in or produced by the human body that has antibodies. The preferred body fluid is blood serum.

Utility

This invention is useful in developing a prognosis for patients known to be immunopositive for HIV. The prognostic test of this invention will allow an early determination as to who is likely to develop AIDS and who is not likely to develop any overt symptoms. As blood screening becomes more prevalent for the presence of HIV, more people will develop psychological stresses, knowing that they are positive for HIV and not knowing if they will develop disease symptoms. The early prognosis can also aid in the early clinical intervention in a case that may not have progressed to the pre-AIDS symptoms.

The kit of the present invention will include an immunoassay for determining the amount of human antibodies in a patient's serum that inhibit HIV reverse transcriptase. The kit will include:

(a) a solution of HIV reverse transcriptase;
(b) a suitable primed RNA template;
(c) suitable nucleoside triphosphates for the synthesis of DNA, including at least one radiolabelled nucleoside triphosphate;
(d) a positive sera control; and
(e) a negative sera control.

The suitable primed RNA template will normally be poly rA:oligo dT. The suitable nucleoside triphosphate for the synthesis of DNA will normally be tritiated dTTP. The nucleoside triphosphate will, of course, have to be the complement of the primed RNA template. If natural RNA is used as primer, that is a natural strand of RNA made of all four bases, then all four deoxyribosipe triphosphates will have to be present. If poly rA is used as the template, the precursor must be dTTP. Poly dT, the complement of poly rA, is then produced in the process of reverse transcription. The poly rA will be primed with a short strand of oligo dT having about 12 to 18 nucleotides at the 3-OH-end of the RNA strand.

The nucleoside triphosphates, primed template, and reverse transcriptase will be in an enzyme reaction buffer. One suitable reaction buffer is 50 mM Tris-HCl, pH 7.9, 5mM dithiotreitol, 0.3mM reduced glutatione, 5mM magnesium chloride, 150 mM potassium chloride, 0.5, mM ethylene gylcol-bis-($\beta$-aminoethylether)N,N,N',N'-tetraacetic acid (hereinafter EGTA), 0.05% triton X-100, 2% ethelyne glycol, 2.5 microgram template primer, and 20 microcuries radiolabelled tritiated dTTP.

The positive sera control is a standard having a known concentration of an antibody inhibiting HIV reverse transcriptase. The negative sera control is normal human serum with no antibodies to HIV. The positive and negative sera controls are used to form a base line. The amount of antibody can be quantitated by comparing the radioactivity detected from the unknown with that detected from the two controls.

The solution of reverse transcriptase, the primed RNA template and nucleoside triphosphate is incubated at between about 30° and 37° C., preferably at 37° C. for between 24 to 48 hours, preferably about 48 hours. The incubation period allows the formation of DNA from the nucleoside triphosphates on the primed RNA template in the presence of reverse transcriptase.

The present invention requires a means for isolating the labelled DNA strand formed, if one has been formed. A preferred method is the precipitation of the DNA. The DNA formed in the preferred embodiment of this invention is poly rA: poly dt. The incubated solution can be passed through a micropourous filter that will allow the passage of the dTTP, but not DNA. One such microporous filter is WHATMAN® GF/A glass microfiber filter. The filter can then be analyzed for retained radioactivity.

Once the DNA has been isolated by any means known to the art, the retained radioactivity is quantitatively detected. The amount of radiation detected is then compared to the amount when the positive and negative controls are used instead of a patient sample.

In practice a sample of patient's serum is tested for the presence of an antibody inhibiting HIV reverse transcriptase by contacting it with the reagents in the kit. If the patient's serum contains an antibody inhibiting HIV to reverse transcriptase, the formation of poly dT will be inhibited or prevented. The amount of antibody inhibiting HIV reverse transcriptase in the patient's serum can be quantitated by comparing to the positive sera control which contains a known amount of antibody to reverse transcriptase. If the patient's serum contains no inhibiting antibodies to reverse transcriptase, the formation of polythymidylic acid will be at nearly the same rate as the negative sera control.

It will be recognized by those skilled in the art that antibodies to HIV reverse transcriptase can be detected by numerous alternative methods known in the art. For example, antibody antigen complexes may be formed and detected using such techniques as ELISA assays, the Western Blot, and the like. However, only those techniques that assay inhibition of HIV reverse transcriptase can be used to detect an antibody inhibiting HIV reverse transcriptase.

This invention also provides a treatment of patients known to be positive for HIV, but negative for an antibody inhibiting HIV reverse transcriptase. The treatment consists of administering amounts of an antibody inhibiting HIV reverse transcriptase to a patient known to be immunopositive for HIV. Such administration will artificially provide the antibody needed to combat further disease by HIV. This treatment can be advantageously used for the treatment of AIDS or pre-AIDS.

HIV reverse transcriptase for use in the kit can be provided either by isolating HIV reverse transcriptase from HIV infected cells, or it can be obtained through genetic engineering techniques.

An antibody inhibiting HIV reverse transcriptase can be provided by isolation from individuals known to produce the antibody from their blood serum. Useful antibodies can also be produced using monoclonal antibody techniques.

We claim:

1. A method of developing a prognosis for a patient known to be immunopostive for HIV comprising:
    contacting a sample of a body fluid of said patient with a solution including HIV reverse transcriptase; primed RNA template; and labeled nucleotide precursor complementary to the primed RNA template;
    incubating the resulting mixture for a predetermined length of time;
    quantitatively detecting the amount of RNA: poly DNA formed;
    making a good prognosis that said patient is unlikely to develop the symptoms of AIDS based on finding an amount of an antibody inhibiting HIV reverse transcriptase, or a poor prognosis that a patient is likely to develop the symptoms of AIDS based on a finding of no antibody inhibiting HIV reverse transcriptase.

2. The method of claim 1 including the step of separating the unreacted labelled nucleotide precursor from any polymers formed.

3. The method of claim 1 including the step of comparing the quantitatively detected amount of labelled poly rA: poly dT in said body fluid with a standard having a known concentration of an antibody inhibiting HIV reverse transcriptase.

4. A kit for developing a prognosis for a patient known to be immunopositive for HIV comprising:

(a) a first container containing HIV reverse transcriptase;
    (b) a second container containing primed RNA template;
    (c) a third container containing nucleoside triphosphate that is complementary to said RNA template for synthesis of DNA;
    (d) a fourth container containing a positive sera control containing a known amount of antibody inhibiting HIV reverse transcriptase; and
    (e) a fifth container containing a negative sera control containing no antibodies to HIV.

5. The kit of claim 4 wherein the primed template is poly rA:oligo dT.

6. The kit of claim 4 including an enzyme reaction buffer including:
    (a) 50 mM Tris-HCl, pH 7.9;
    (b) 5mM dithiotreithol;
    (c) 0.3 mM reduced glutathione;
    (d) 5 mM magnesium chloride;
    (e) 150 mM potassium chloride;
    (f) 0.5 mM EGTA;
    (g) 0.05% nonionic surfactant; and
    (h) 2% ethylene glycol.

7. The kit of claim 4 wherein the nucleoside triphosphate is tritiated dTTP and poly rA: poly dT is the form of DNA synthesized.

8. The kit of claim 7 including a means to precipitate poly rA: poly dT on a microporous filter that allows the passage of dTTP but not the passage of poly rA: poly dT.

9. A kit for developing a prognosis for a patient known to be immunopositive for HIV comprising:
    (a) a first reagent container containing HIV reverse transcriptase;
    (b) a second container containing a primed RNA template and a nucleoside triphosphate that is complementary to said RNA template;
    (c) a third reagent container containing a positive sera control containing an known amount of antibody inhibiting HIV reverse transcriptase; and
    (d) a fourth container containing a negative sera control containing no antibodies to HIV.

10. The kit of claim 9 wherein said first reagent container and said second reagent container contain solutions of enzyme reactive buffer.

11. The kit of claim 10 wherein said enzyme buffer includes:
    (a) 50 mM Tris-HCl, pH 7.9;
    (b) 5mM dithiotreithol;
    (c) 0.3 mM reduced glutathione;
    (d) 5 mM magnesium chloride;
    (e) 150 mM potassium chloride;
    (f) 0.5 mM EGTA;
    (g) 0.5% triton X-100; and
    (h) 2% ethylene glycol.

* * * * *